United States Patent [19]

Berman

[11] 4,069,820
[45] Jan. 24, 1978

[54] INTUBATING PHARYNGEAL AIRWAY

[76] Inventor: Robert A. Berman, 501 Cedar Hill Road, Far Rockaway, N.Y. 11691

[21] Appl. No.: 777,642

[22] Filed: Mar. 15, 1977

Related U.S. Application Data

[62] Division of Ser. No. 708,274, July 23, 1976.

[51] Int. Cl.² .................................... A61M 16/00
[52] U.S. Cl. ...................................... 128/208; 128/351
[58] Field of Search ............... 128/206, 208, 343, 345, 128/348–351

[56] References Cited

U.S. PATENT DOCUMENTS 3,908,665  9/1975  Moses .................................. 128/351
3,930,507  1/1976  Berman ............................... 128/351

FOREIGN PATENT DOCUMENTS 1,345,518  12/1963  France ................................ 128/351
   83,331   6/1964  France ................................ 128/351

*Primary Examiner*—Dalton L. Truluck
*Attorney, Agent, or Firm*—Stoll and Stoll

[57] ABSTRACT

A intubating pharyngeal airway having a side access for passage of a tube on the said airway comprising a flanged stop at the proximal end, a curved airway central tubular member and a distal ball tip adapted to fit into the vallecular. The side opening may be expanded or closed by means of either a hinge on the opposite side wall of the tube or by a cap or insert closure.

2 Claims, 32 Drawing Figures

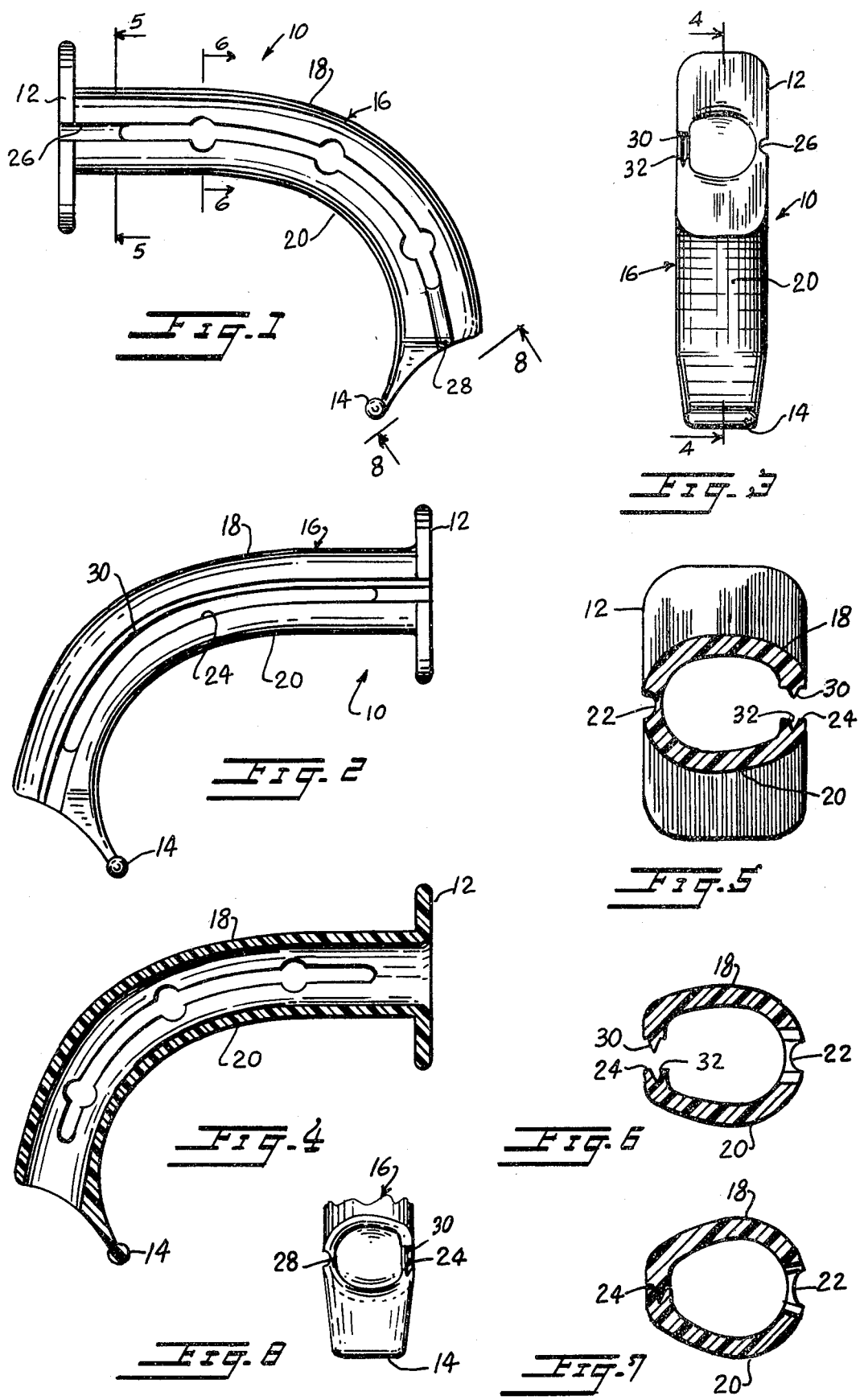

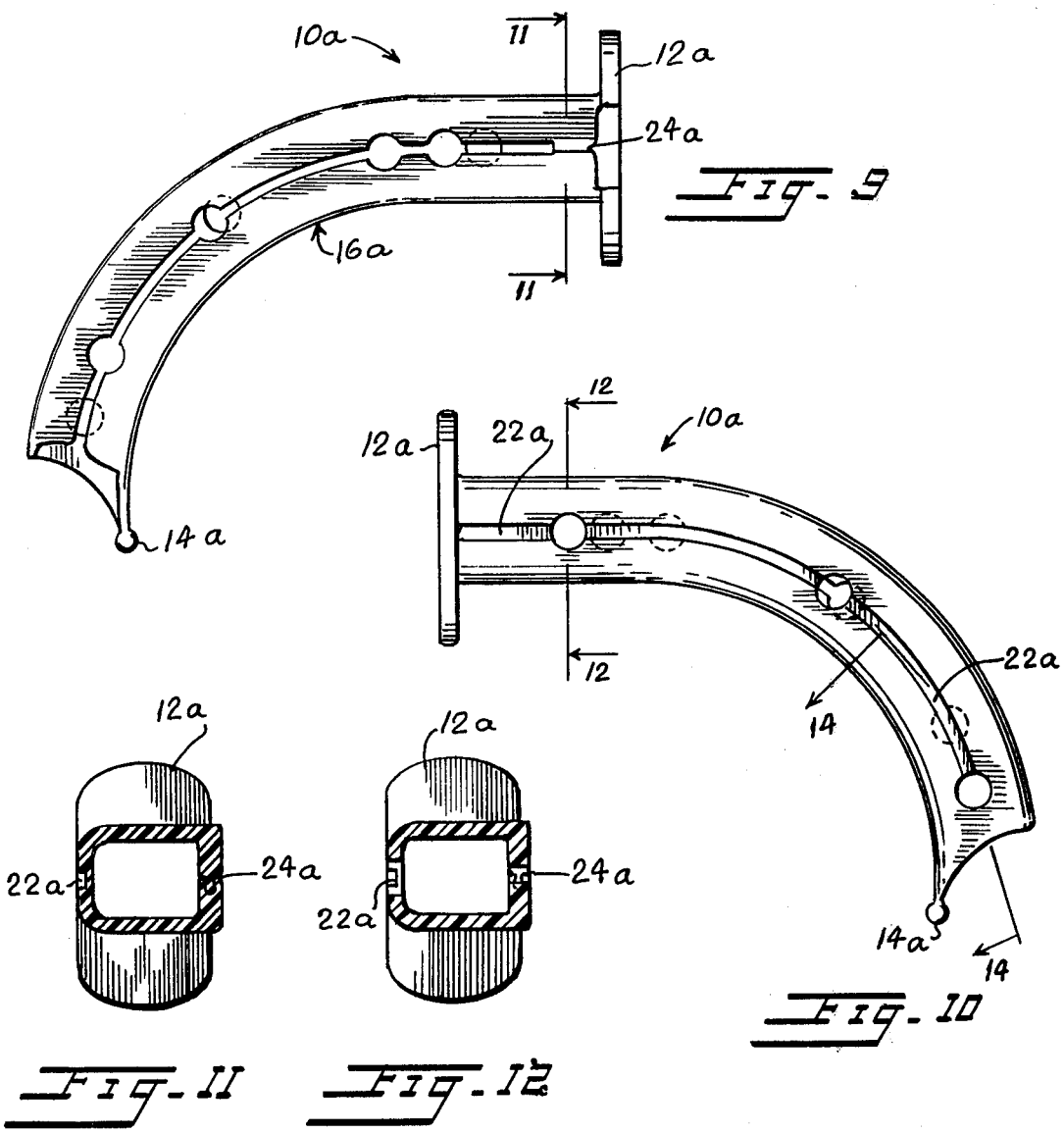
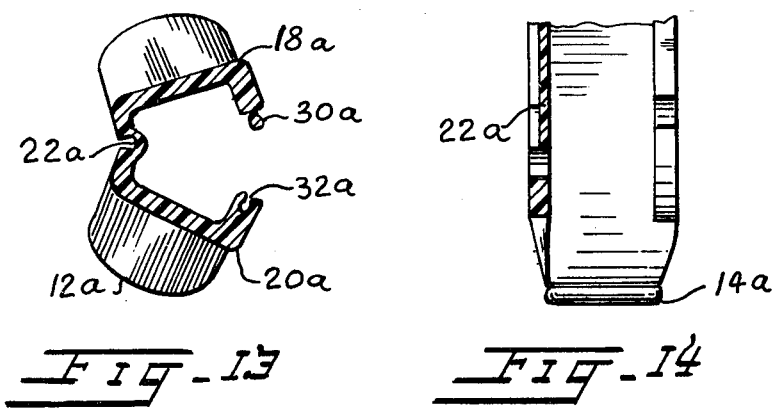

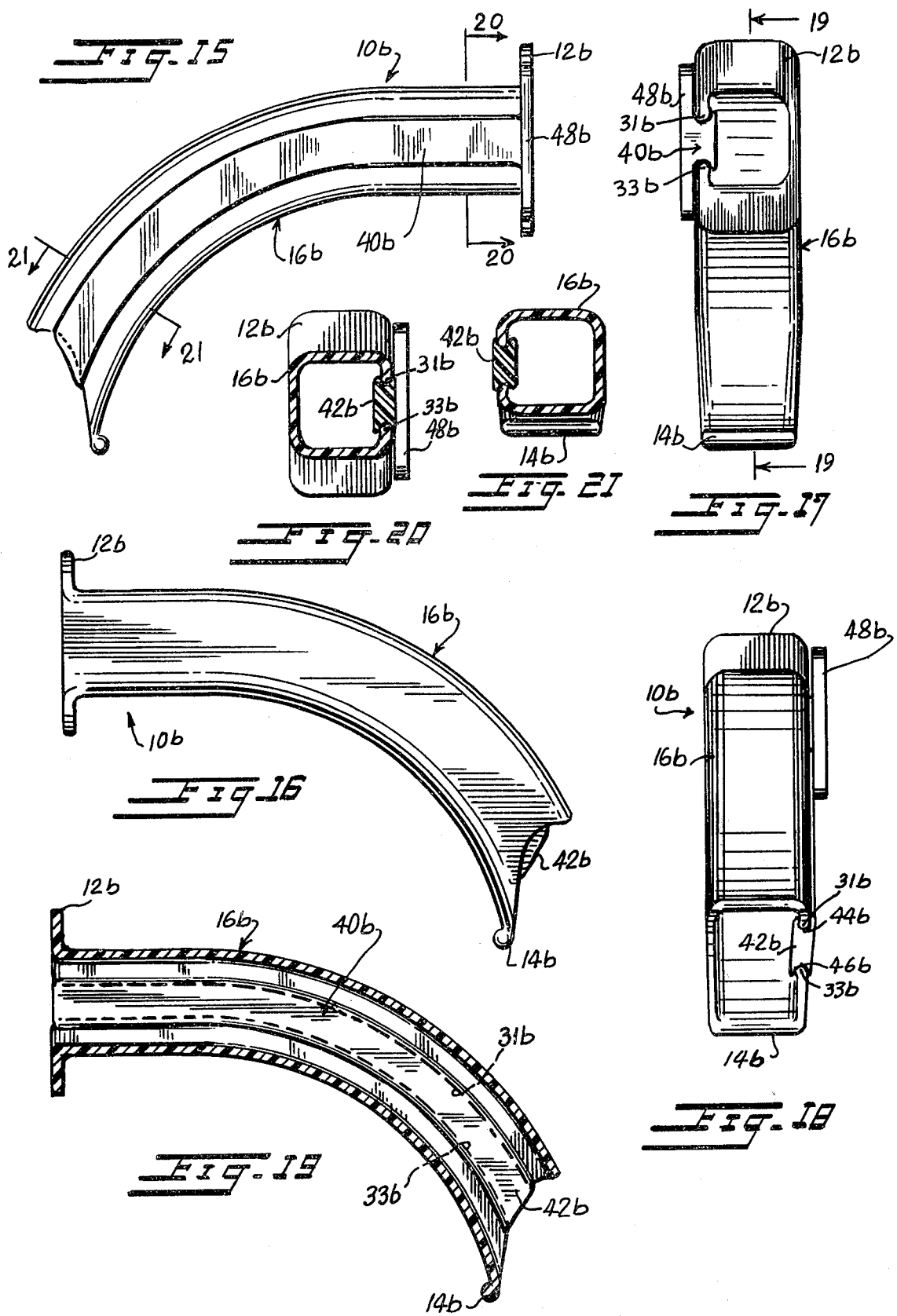

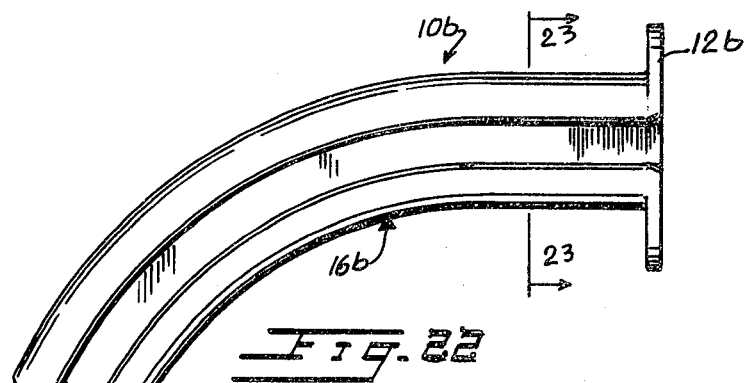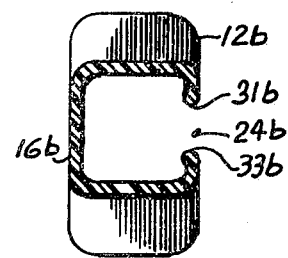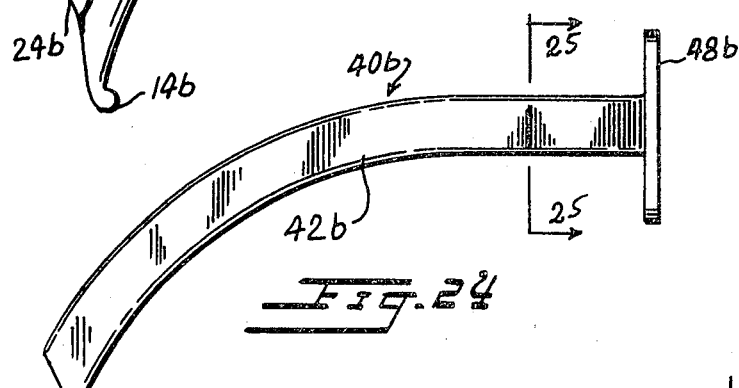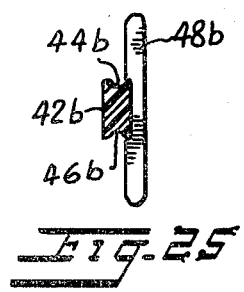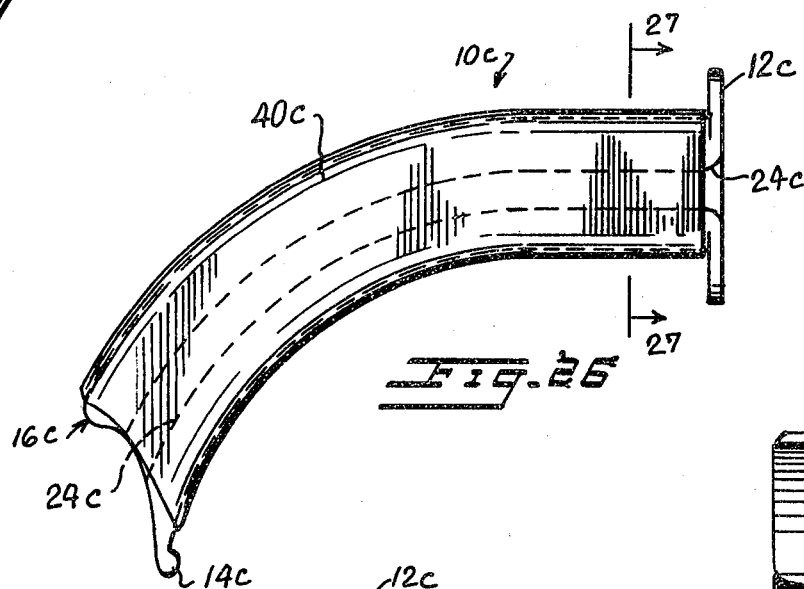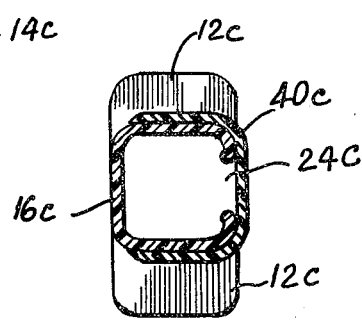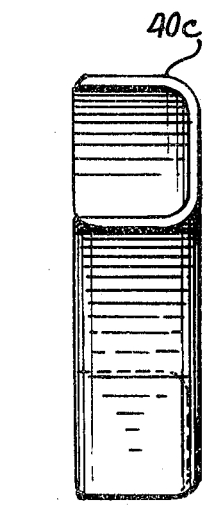

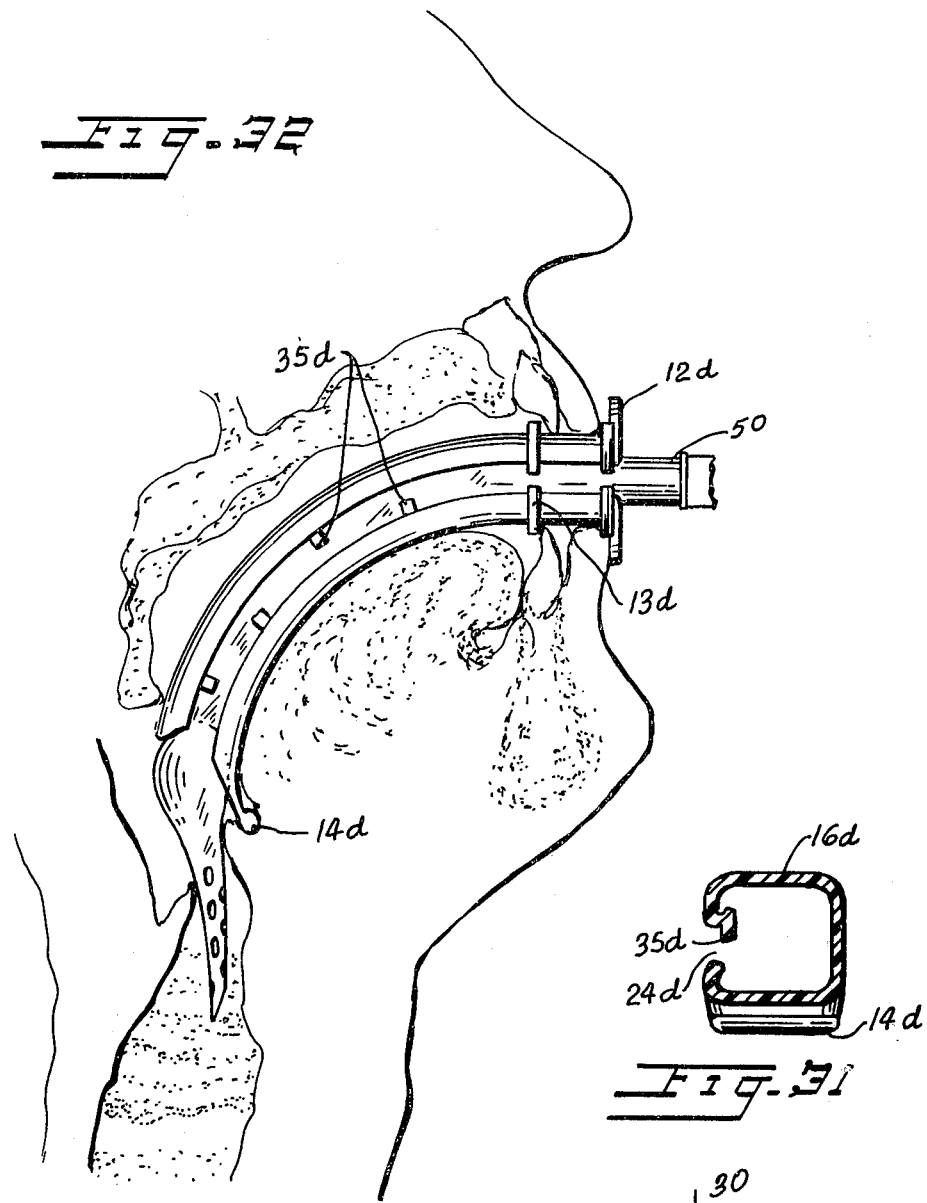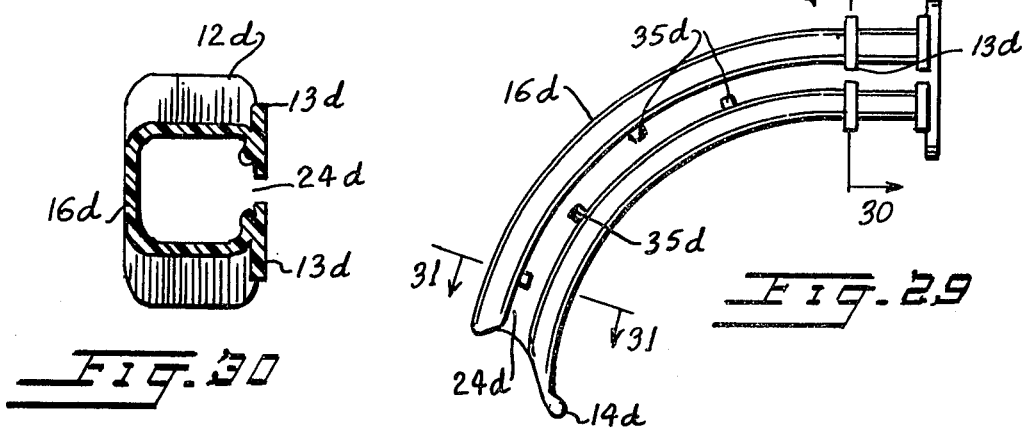

INTUBATING PHARYNGEAL AIRWAY

This application is a divisional of copending U.S. patent application Ser. No. 708,274, filed July 23, 1976, and entitled Intubating Pharyngeal Airway. In addition, this application is related to copending U.S. patent application Ser. No. 750,739, filed Dec. 15, 1976, and Ser. No. 777,641, filed even date herewith, and each being a divisional of said application Ser. No. 708,274.

REFERENCE TO RELATED DOCUMENTS

Reference is made to Berman U.S. Pat. No. 3,930,507 issued Jan. 6, 1976 for an adjustable oral airway, to Berman U.S. Pat. No. 2,599,521 issued June 3, 1952 for a respiratory device and to the references cited in each patent. The proximal location of an airway with respect to the pharynx, epiglottis, vallecular and trachea of a patient may be seen in FIG. 10 of Berman U.S. Pat. No. 3,930,507.

BACKGROUND OF THE INVENTION

The device shown in Berman U.S. Pat. No. 2,599,521 is used for the purposes of aiding the breathing of anesthetized or otherwise unconscious patients and such device is now well-known in the medical profession as the Berman Oral Airway. The Berman Oral Airway, and later devices modeled thereafter, is employed in the practice of surgery and medicine by insertion into the mouth and pharynx of a patient to provide a channel for respiratory purposes.

The adjustable oral airway of Berman U.S. Pat. No. 3,930,507 shows an airway having two sections slideable with respect to each other and joined at the distal end.

SUMMARY OF THE INVENTION

The Berman Intubating Pharyngeal Airway of the present invention briefly, but not by way of limitation, provides a tubular airway having an openable side to allow passage of appropriate medical and surgical appliances, such as an endotracheal tube, into the larynx and trachea without the use of a laryngoscope. The side opening airway permits blind oral intubating of the larynx and esophagus with ease even in difficult cases of cardiopulmonary-resuscitation and anesthetic procedures.

The intubating airway is designed to place an endotracheal tube into the larynx and trachea while at the same time providing an adequate pharyngeal airway itself.

The lateral opening at the side of the airway allows the airway to be removed from the mouth, leaving endotracheal tube in place. The airway is designed primarily to place the endotracheal tube into the trachea and at the same time provide adequate pharyngeal airway by itself. The extra large lumen of the airway separates the tongue from the pharynx allowing a wider unobstructed air passageway from the lips to the larynx.

BRIEF DESCRIPTION OF THE DRAWING

FIG. 1 is a side view of a preferred embodiment of the intubating airway of the present invention, showing the hinge side.

FIG. 2 is a view of the opposite side of the intubating airway of FIG. 1 showing the longitudinal side opening.

FIG. 3 is a proximal end view of the intubating airway of FIG. 1.

FIG. 4 is a cross-sectional view taken across line 4—4 of FIG. 3.

FIG. 5 is an enlarged cross-sectional view taken across line 5—5 of FIG. 1.

FIG. 6 is an enlarged cross-sectional view taken across line 6—6 of FIG. 1.

FIG. 7 is a cross-sectional view similar to that of FIG. 6 but showing the airway in its closed position.

FIG. 8 is a fragmentary distal end view as seen across line 8—8 of FIG. 1.

FIG. 9 is a side view of a first modified embodiment of the intubating airway of the present invention. The side opening is visible.

FIG. 10 is a view of the opposite, hinge side of the intubating airway of FIG. 9.

FIG. 11 is a cross-sectional view taken across line 11—11 of FIG. 9.

FIG. 12 is a cross-sectional view taken across line 12—12 of FIG. 10.

FIG. 13 is a view similar to that of FIG. 11 but showing the airway in its open position.

FIG. 14 is a cross-sectional view taken across line 14—14 of FIG. 10.

FIG. 15 is a side view of a second modified embodiment of the intubating airway of the present invention.

FIG. 16 is a view of the opposite side of the intubating airway shown in FIG. 15.

FIG. 17 is a proximal end view of the intubating airway shown in FIG. 15.

FIG. 18 is a rear view of the intubating airway shown in FIG. 15.

FIG. 19 is a cross-sectional view taken in line 19—19 of FIG. 17.

FIG. 20 is a cross-sectional view taken across line 20—20 of FIG. 15.

FIG. 21 is a cross-sectional view taken across line 21—21 of FIG. 15.

FIG. 22 is a view similar to that of FIG. 15 with the plug closure removed.

FIG. 23 is a cross-sectional view taken across line 23—23 of FIG. 22.

FIG. 24 is a side view of the plug closure shown in FIG. 15.

FIG. 25 is a cross-sectional view taken across line 25—25 of FIG. 24.

FIG. 26 is a side view of a third modified embodiment of the intubating airway of the present invention.

FIG. 27 is a cross-sectional view taken across line 27—27 of FIG. 26.

FIG. 28 is a proximal end view of the cap closure of the third modified embodiment as shown in FIG. 26.

FIG. 29 is a side view of a fourth modified embodiment of the intubating airway of the present invention.

FIG. 30 is a cross-sectional view taken across line 30—30 of FIG. 29.

FIG. 31 is a cross-sectional view taken across line 31—31 of FIG. 29.

FIG. 32 is a view of the embodiment of the intubating airway of FIG. 29 shown in place in the mouth of a patient with an endotracheal tube positioned therethrough. The patient is shown in partial sagittal section.

DESCRIPTION OF THE INVENTION

With reference to the drawing, a preferred embodiment of the invention is shown in FIGS. 1-8 and comprises a intubating airway 10 having a flanged proximal end 12 and an enlarged rounded distal end 14 with an intermediate curved tubular section 16 between the proximal and distal ends.

Tubular section 16 is substantially uniform in cross-section and comprises two longitudinal sections 18 and 20 joined on one side of tube 16 by a hinge 22 and having a mating opening 24 extending longitudinally of tube 16 on the opposite side thereof from hinge 22. A longitudinal opening 24 extends fully from end to end of intubating airway 10, including the proximal and distal ends thereof, whereby the airway may be opened or closed at longitudinal opening 24 by rotation about hinge 22. This feature may be seen in a comparison of FIGS. 6 and 7.

Intubating airway 10 may be molded of a suitable autoclaveble material sufficiently rigid to maintain its shape and sufficiently plastic to permit flexibility in each and in opening and closing longitudinal opening 24. In particular, hinge 22 may be a molded hinge having an outer flex portion 26 adjacent proximal end 12 and an inner flex portion 28 adjacent distal end 14. Due to the longitudinal curvature of tube 16, it will be noted that upper and lower hinge members 26 and 28, respectively, are not co-axially aligned and hinge 22 accordingly has a degree of flexibility and plasticity to enable opening and closing of longitudinal opening 24.

Longitudinal opening 24 has a tongue and groove closure wherein tongue 30 is an integral part of upper section 18 and mating groove 32 is an integral part of and is defined in lower section 20.

With reference now to the first modified embodiment of the invention as shown in FIGS. 9-14, intubating airway 10a comprises an integral flanged proximal end 12a, an expanded integral ball distal end 14a and a longitudinally curved tubular mid-section 16a having a longitudinally extending open side 24a and an opposite hinge side 22a, all substantially similar to similar portions of the preferred embodiment.

Longitudinal opening 24a is a snap-closure comprising a longitudinal male member 30a formed integrally with upper section 18a of tube 16a and a longitudinal female member 32a formed and defined in lower section 20a of tube 16a. The snap-closure and opening may be seen in a comparison of FIGS. 11 and 13.

A second modified embodiment of the invention is shown in FIGS. 15-25. Intubating airway 10b comprises an integral flanged proximal end 12b, an inner expanded rounded distal end 14b and an intermediate longitudinal curved tubular section 16b having a longitudinal opening 24b along one side thereof. Longitudinal opening 24b is large enough to pass laterally such suitable surgical and medical devises as an endotracheal tube 50 such as is shown in FIG. 32 in connection with another embodiment. Longitudinal opening 24b does not close by hinge action as is the case in the former embodiments and there is no hinge member per se in the present embodiment although the inherent flexibility of the material from which intubating airway 10b is molded will yield some degree of variability in the transverse dimension of longitudinal opening 24b. In the present embodiment, longitudinal opening 24b may be closed by a longitudinal plug closure 40b which is adapted to snap laterally or slide longitudinally into longitudinal opening 24b and thereby close the same. Plug closure 40b comprises a longitudinal body section 42b having upper end lower grooves 44b and 46b, respectively, to engage upper and lower jaws 31b and 33b, respectively, of longitudinal opening 24b. The main body portion 42b is longitudinally curved in accordance with longitudinal curvature of tubular section 16b and is provided with a flanged outer end 48b which acts as a handle for ease of insertion or removal of plug closure 40b with respect to longitudinal opening 24b. As with flanged proximal end 12b, flanged outer end 48b has the additional function of being a bite block which helps to secure the laryngoscopic intubating airway at the patient's mouth to prevent undesirable inward displacement thereof down the patient's throat.

A third modified embodiment of the invention is shown in FIGS. 26-28 and comprises intubating airway 10c, substantially similar to intubating airway 10b of the second modified embodiment, having a similar flanged proximal end 12c, an expanded rounded distal tip 14c and an intermediate longitudinally curved tubular member 16c having a longitudinal opening 24c along one side thereof.

A cap closure 40c is provided to close opening 24c by securing over the outside of tubular member 16c. Cap closure 40c is accordingly a channel member having a substantially U-shaped cross-section and is curved longitudinally in accordance with the curvature of tubular portion 16c.

A fourth modified embodiment is shown in FIGS. 29-32 and comprises a intubating airway 10d having a flanged proximal end 12d, an expanded rounded distal end 14d and an intermediate longitudinally curved tubular section 16d having a longitudinal opening 24d, along one side thereof. Extending into longitudinal opening 24d, and partially obstructing the same, are a plurality of retaining pins 35d which are preferrably molded integrally with tubular portion 16d. It is the function of retaining pins 35d retain a tube such as endotracheal tube 50 from unwanted lateral displacement through opening 24d or, conversely, to prevent unwanted lateral displacement of intubating airway 10d with respect to endotracheal tube 50. Retaining pins 35d are provided with a degree of flexibility sufficient to permit lateral passage of endotracheal tube 50 into or out of opening 24d when so intended and manually manipulated by qualified personnel. Retaining pins 35d obviate the need for other closure members and opening 24d but, nevertheless, such a closure member as cap closure 40c may be provided if desired.

Also shown in connection with the fourth embodiment is a second set of flanges 13d located on tubular member 16d a spaced distance from proximal end 12d, the function of all such flanges being to locate the intubating airway against longitudinal displacement with respect to the patient's mouth and throat. As may be seen in FIG. 32, flanged proximal end 12d engages against the patient's lips to limit inward displacement of the airway while flanges 13d lock inside patient's teeth to prevent unwanted outward displacement of the airway. It may be seen that the tubular construction of the airway together with the side opening thereof provides an airway of unparalleled usefulness.

While the foregoing is illustrative of preferred and modified embodiments of the invention it is clear that other modifications may be had within the scope of the invention.

A preferred material from which the airway may be molded or otherwise formed is polyethylene.

What is claimed is:
1. An intubating airway, comprising:
 a. a tubular longitudinally extending body member said body member having a longitudinally extending side opening, defined therein, b. said member having a distal end for insertion into the mouth and throat of a patient and a proximal end for location at the mouth of the patient, and c. a cap closure member, said cap closure member comprising a U-shaped channel removably engaged and secured over said body member at said side opening to cover said longitudinally extending side opening.

2. An intubating airway in accordance with claim 1, wherein the length of said cap closure member is substantially the length of said longitudinally extending side opening.

* * * * *